United States Patent
Inderbitzen et al.

[11] Patent Number: 5,484,411
[45] Date of Patent: Jan. 16, 1996

[54] SPIRAL SHAPED PERFUSION BALLOON AND METHOD OF USE AND MANUFACTURE

[75] Inventors: Mark Inderbitzen, Miramar; Susana Martinez, Pembroke Pines, both of Fla.

[73] Assignee: Cordis Corporation, Miami Lakes, Fla.

[21] Appl. No.: 182,729

[22] Filed: Jan. 14, 1994

[51] Int. Cl.⁶ ............................................. A61M 29/00
[52] U.S. Cl. ..................................... 604/96; 606/194
[58] Field of Search ............................... 604/96, 97, 53, 604/100, 101, 102, 103; 606/191–194

[56] References Cited

U.S. PATENT DOCUMENTS

| | | |
|---|---|---|
| 3,889,686 | 6/1975 | Duturbure . |
| 4,183,102 | 1/1980 | Guiset . |
| 4,233,983 | 11/1980 | Rocco . |
| 4,423,725 | 1/1984 | Baran et al. . |
| 4,447,227 | 5/1984 | Kotsanis . |
| 4,581,017 | 4/1986 | Sahota . |
| 4,585,000 | 4/1986 | Hershenson . |
| 4,641,653 | 2/1987 | Rockey . |
| 4,694,827 | 9/1987 | Weiner et al. . |
| 4,723,549 | 2/1988 | Wholey et al. . |
| 4,762,130 | 8/1988 | Fogarty et al. . |
| 4,763,653 | 8/1988 | Rockey . |
| 4,771,777 | 9/1988 | Horzewski et al. . |
| 4,787,388 | 11/1988 | Hofmann . |
| 4,790,315 | 12/1988 | Mueller, Jr. et al. . |
| 4,795,427 | 1/1989 | Helzel . |
| 4,820,271 | 4/1989 | Deutsch . |
| 4,832,028 | 5/1989 | Patel . |
| 4,857,054 | 8/1989 | Helfer . |
| 4,877,031 | 10/1989 | Conway et al. . |
| 4,878,495 | 11/1989 | Grayzel . |
| 4,892,519 | 1/1990 | Songer et al. . |
| 4,909,252 | 3/1990 | Goldberger . |
| 4,983,167 | 1/1991 | Sahota . |
| 5,000,734 | 3/1991 | Boussignac et al. . |
| 5,000,743 | 3/1991 | Patel . |
| 5,006,119 | 4/1991 | Acker et al. . |
| 5,019,042 | 5/1991 | Sahota . |
| 5,035,694 | 7/1991 | Kasprzyk et al. . |
| 5,046,503 | 9/1991 | Schneiderman . |
| 5,078,685 | 1/1992 | Colliver . |
| 5,087,247 | 2/1992 | Horn et al. . |
| 5,090,958 | 2/1992 | Sahota . |
| 5,090,960 | 2/1992 | Don Michael . |
| 5,108,370 | 4/1992 | Walinsky . |
| 5,129,883 | 7/1992 | Black . |
| 5,135,474 | 8/1992 | Swan et al. . |
| 5,137,513 | 8/1992 | McInnes et al. . |
| 5,147,377 | 9/1992 | Sahota . |
| 5,152,277 | 10/1992 | Honda et al. . |
| 5,160,321 | 11/1992 | Sahota . |
| 5,181,911 | 1/1993 | Shturman . |
| 5,195,955 | 3/1993 | Don Michael . |
| 5,195,971 | 3/1993 | Sirhan . |
| 5,222,941 | 6/1993 | Don Michael . |
| 5,226,888 | 7/1993 | Arney . |
| 5,232,446 | 8/1993 | Arney . |
| 5,261,879 | 11/1993 | Brill . |
| 5,295,959 | 3/1994 | Gurbel et al. ............... 604/96 |

FOREIGN PATENT DOCUMENTS

| 8102110 | 6/1981 | WIPO ........................ 604/96 |
| WO93/17748 | 9/1993 | WIPO . |

Primary Examiner—J. Yasko
Attorney, Agent, or Firm—Lockwood, Alex, Fitzgibbon & Cummings

[57] ABSTRACT

A dilation catheter suitable for use in medical procedures is provided. The catheter includes a balloon disposed on an elongated tube. The tube is capable of passing fluid between the balloon and the tube for varying the balloon between an inflated expanded condition and a deflated collapsed condition. The balloon includes a longitudinally extending spiral wall which forms a longitudinally extending spiral channel spaced inwardly from the exterior surface of the balloon when the balloon is in its expanded condition to allow fluid to be perfused past the balloon.

13 Claims, 1 Drawing Sheet

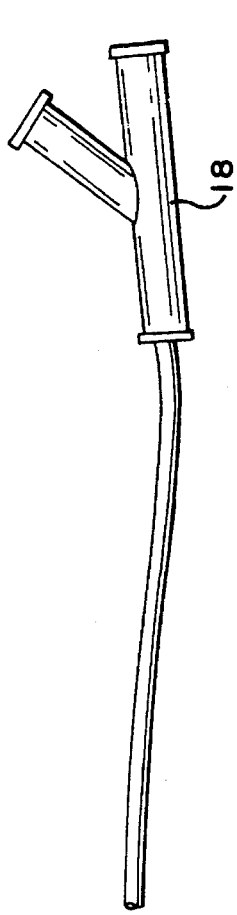
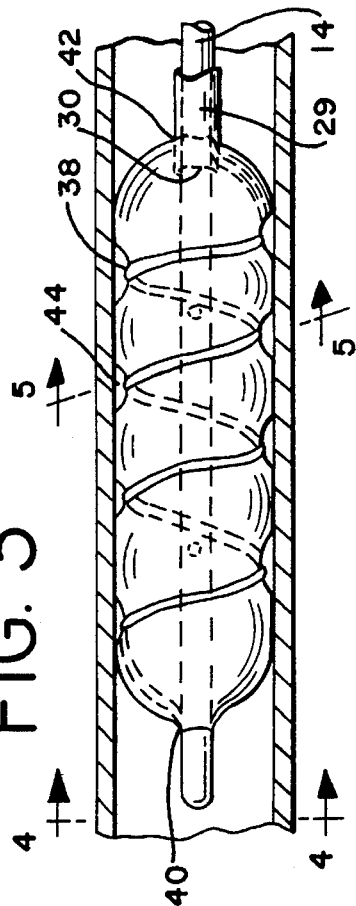
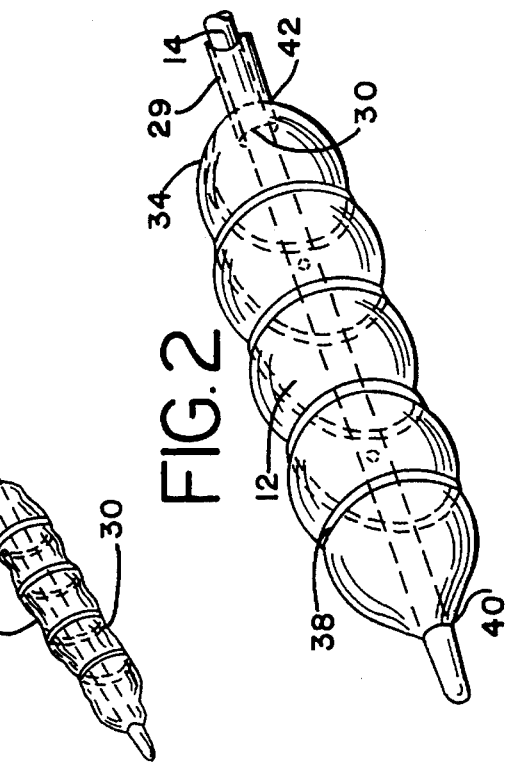
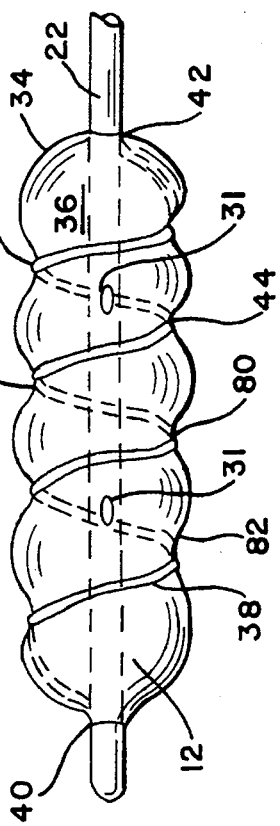
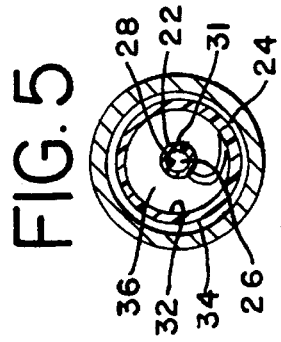
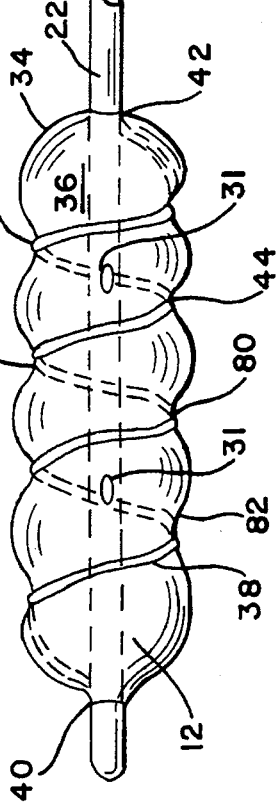

5,484,411

SPIRAL SHAPED PERFUSION BALLOON AND METHOD OF USE AND MANUFACTURE

The present invention relates generally to dilation catheters suitable for percutaneous transluminal coronary angioplasty procedures (PTCA), and more particularly to dilation catheters for use in PTCA procedures wherein blood is perfused distally of the dilation balloon during the inflation cycle of the balloon.

BACKGROUND AND SUMMARY OF THE INVENTION

PTCA procedures generally include inflation of a balloon in an arterial passage in an effort to clear a flow path for blood by dilating the stenosis. Inflation of the balloon and subsequent deflation and removal of the balloon results in treatment of the stenosis to increase the available cross-sectional area for blood to flow through the arterial passage.

In typical PTCA procedures, a guiding catheter is inserted into the cardiovascular system through the Tee-brachial or femoral arteries, generally under local anesthesia, until the distal tip of the catheter is in a coronary artery and generally positioned adjacent a stenosis. An extensible balloon of a dilation catheter is advanced through the guiding catheter alone or over a previously introduced guidewire until the balloon is positioned across the stenosis. The balloon is then inflated to a predetermined size with a fluid, preferably a radiopaque liquid, to radially compress the inside of the artery wall, thereby dilating the lumen of the artery. The balloon is then deflated so that the dilation catheter can be removed, and blood flow. resumed through the dilated artery that now has a larger cross-sectional area to permit a greater volume of blood to flow therethrough.

In typical PTCA procedures, when the balloon of a dilation catheter is inflated in a coronary artery, all flow ceases through the coronary artery. If blood flow ceases for too long a period of time, the part of the heart and associated sidebranches which that coronary artery serves can begin to suffer from lack of blood, or ischemia. If the balloon remains inflated in the artery for prolonged periods of time, the injury caused by the absence of blood flow can be irreversible in some cases. On the other hand, it has been found that the probability of an artery wall or the stenosis maintaining its dilated cross-sectional area after having been subjected to dilation from an extensible balloon is directly related to the length of time that the balloon is inflated while located across the stenosis. However, the aforementioned potential problems associated with blocking blood flow are increased the longer the balloon is inflated in the artery.

Attempts have been made to produce dilation catheters that perfuse blood through a catheter or balloon when the balloon is inflated to avoid ischemia conditions distally of the balloon. For example, Wijay, et al., U.S. Pat. No. 5,158,540, discloses a perfusion catheter that perfuses blood during the balloon's inflation cycle to allow for longer inflation periods; however, the catheter is extremely complicated structurally and expensive to manufacture. Also, current perfusion catheters which require a channel within the balloon for blood flow increase the crossing profile.

It is, therefore a general object of the present invention, to provide a new and improved perfusion balloon dilation catheter suitable for PTCA procedures.

Another object of the invention is to provide a dilation catheter suitable for PTCA procedures wherein the catheter perfuses blood around the inflated balloon and permits prolonged inflation times for the balloon.

Yet another object of the present invention is to provide a dilation catheter of a relatively simple structure for use in PTCA procedures where blood is perfused distally of the inflated balloon and to sidebranches of the vessel which may be contacted by the balloon.

Another object of this invention is to provide an improved perfusion balloon catheter which exhibits a low crossing profile.

The present invention overcomes the problems associated with the prior art perfusion catheters by providing a perfusion balloon catheter having a dilation balloon member with an exterior and interior surface disposed on a flexible tubular member. A portion of the exterior surface includes a longitudinally extending spiral wall forming a longitudinally extending spiral channel. The balloon may be varied between a collapsed condition of a size allowing the catheter to be transported through a body vessel and an expanded condition of a size allowing the exterior surface to engage a body vessel wall. The spiral wall is spaced radially inwardly from the exterior surface when the balloon is in its expanded condition allowing blood to be perfused past the balloon.

For a complete understanding of the present invention, reference is made to the embodiments illustrated in greater detail in the accompanying drawings and described by way of example. It should be understood that this invention is not limited to the particular embodiments illustrated herein, but is defined by the appended claims.

BRIEF DESCRIPTION OF THE DRAWINGS

FIG. 1 is a perspective view of a balloon catheter made according to the present invention;

FIG. 2 is an enlarged perspective view of a portion of the catheter of FIG. 1;

FIG. 3 is an elevational view of the catheter of FIG. 2 disposed within a body vessel, shown in cross-section;

FIG. 4 is an end view of the catheter of FIG. 3 taken along line 4—4;

FIG. 5 is a cross-sectional view of the catheter of FIG. 3 taken along line 5—5; and FIG. 6 is a side elevational view of the catheter of FIG. 2 including an external membrane.

DETAILED DESCRIPTION OF THE PREFERRED EMBODIMENT

While the invention may be embodied in a variety of forms and used in different applications such as angioplasty, valvuloplasty, and urological uses, a description of one preferred embodiment of the inventive concept will be made in the form of a dilation catheter for use in percutaneous transluminal coronary angioplasty procedures. As illustrated in the drawings, the perfusion balloon catheter, generally designated at 10 in FIG. 1, made according to the present invention comprises an extensible balloon 12 located substantially near the distal end of an elongated flexible tubular shaft 14. The illustrated catheter includes a hub 18, of a type well known in the art. Any suitable fitting and/or hub can be provided as desired. It should be understood that the present invention may be used on fixed-wire, over-the-wire, and monorail type balloon catheters.

A coaxial lumen type of catheter arrangement is shown in FIG. 4. A lumen 20 of tubular shaft 14 can accommodate a guidewire and may be of a substantially small diameter similar to that of the outer diameter of a standard guidewire, preferably having a diameter of between about 0.008 inch and about 0.022 inch. Coaxial passageway 30 between tubular shaft 14 and outer shaft 29 is utilized for carrying fluid, such as radiopaque saline solution or other fluid of a type well known in the art. The fluid carried by passageway 30 is communicated to balloon 12 for inflating and deflating balloon 12. It should be understood that the passageway 30 is large enough to carry adequate amounts of fluid for inflating balloon 12 sufficiently quickly.

An alternate embodiment of the flexible tubular shaft 22 is shown in FIG. 5 and illustrates a dual lumen catheter 24, including lumen 26 and lumen 28. As illustrated, lumen 26 is substantially larger in cross-sectional area than lumen 28 and may be utilized to carry fluid to and from balloon 12 similarly to that of lumen 20. Lumen 28 may be utilized to receive a guidewire to provide assistance in placing the dilation catheter at the appropriate position in a body vessel. Fluid is communicated to the interior of the balloon through openings 31. It is preferred that the openings 31 be slits that extend longitudinally with the flexible tube to prevent propagation of the openings while the tube is being manipulated during insertion into a body vessel. Other shapes of openings and connections, such as circular openings, may also be utilized to pass fluid between the tubing shaft and the interior of the balloon 12. Any number of such openings may be utilized to pass fluid between the flexible tube and the interior of the balloon 12. Alternatively, a separate lumen may extend from the proximal end of the catheter terminating at the proximal end of the balloon to pass fluid into and out of the interior compartment of the balloon to inflate and deflate the balloon.

Flexible tubing utilized in the present invention is preferably formed of a suitable thermoplastic material, such as polyethylene, polyvinylchloride, nylon, polyethylene terephthalate, polyurethane and the like, or from a composite structure.

The balloon 12 is generally cylindrically shaped and includes an inner surface 32 and an exterior surface 34. The balloon is in seal providing communication about its outer body and respective edges to the flexible tube, defining an interior compartment 36. The balloon may be inflated to an expanded condition by the introduction of fluid into interior compartment 36. When fluid is removed from interior compartment 36 the balloon returns to a collapsed condition.

The balloon includes a longitudinally extending spiral wall 38 extending from the distal end 40 to the proximal end 42 of the balloon. The wall 38 is preferably formed integrally with the balloon exterior surface and is formed by inflating the balloon to its expanded position and then radially restricting the expansion of the balloon along a longitudinally extending spiral path and thereafter setting the balloon, for example, by heat setting, chemically setting, photodynamically setting, frequency setting and the like. For example, a generally cylindrical balloon in a collapsed condition may be inserted into a stretched tension spring or other helically shaped constraining device. Once positioned in the spring, the balloon is inflated to its expanded condition. It should be understood that in this example, the diameter of the spring or the like is less than the diameter of the expanded balloon, thus portions of the exterior surface of the balloon engaging the spring will be restricted and prevented from expanding outwardly to the balloon's maximum inflated diameter. When in this position, the balloon is set by heat or other setting means or thermoformed by maintaining it at an elevated temperature until the selected material is thermally set. Tailorability that is achieved is a function of the particular heat setting conditions. The setting temperature can vary with the type of material used, wall thickness, and the treatment time. Some thermosetting material that may be utilized include, for example, natural latex rubber, a cross-linked or non cross-linked polyethylene, polyethylene terephthalate, polyurethane or a silicone rubber. Nylons and/or polyamides may also be selected. Once these materials are set, they cannot be heat deformed again under normal conditions to which these types of catheters are subjected.

As a result of its formation in the spring or other constraining device, balloon 12 includes a longitudinally extending spiral channel 44 spaced radially inwardly from the exterior surface of the balloon when the balloon is in its expanded condition. The size of the channel may be varied by utilizing a spring or springs or the like presenting different diameters to form the channel radially inward from the exterior surface.

In addition, the balloon may include a membrane 80 or a sheath (FIG. 6) disposed over the channels by heat sealing the membrane to the body of the balloon, or by utilizing an adhesive. The membrane is utilized to help minimize the filling in of the channel 44 by stenotic material and to help make the angioplasty more uniform. In some instances, it may be desirable to include openings or perforations 82 through the membrane or sheath 80 where side branch perfusion is of particular concern.

The flexible tubular shaft 22 extends through the interior compartment of balloon 12. This allows the flexible tube to pass fluid into interior compartment 36 through openings 31. It should be understood that the lumen carrying fluid through the flexible tube 22 does not extend through the distal end of the tube 22; otherwise fluid would exit the tube into the body vessel and not be forced through openings 31 into the interior compartment 36. When balloon 12 is inflated to its expanded condition by the introduction of fluid into interior compartment 36, the exterior surface 34 expands radially outwardly from flexible tubular shaft 22. When fluid is removed from the interior compartment, exterior surface 34 is substantially adjacent tube 22 and the balloon 12 is in a substantially collapsed state.

In a typical operation, catheter 10 is generally advanced from the femoral artery or the Tee-brachial artery up the aortic root and is positioned in the appropriate coronary artery or peripheral body vessel. Advancement of the catheter through an artery or body vessel is preferably performed when the balloon is in its collapsed, non-inflated condition. The balloon which is disposed at the distal end of the catheter is positioned across a restriction or stenosis in the artery. Thereafter, the balloon is inflated in the artery by pumping fluid through lumen of the flexible tubing. Inflation of the balloon causes the balloon to radially expand causing exterior surface to engage the artery wall or stenosis and dilate the artery wall. Balloon 12 may remain in its expanded condition for a considerably longer time than conventional catheters because the blood is perfused past the balloon and also into sidebranches through longitudinally extending spiral channel 44 without need for a separate mechanism to pump or channel the blood.

One advantage of the spiral geometry of the balloon of the present invention is that the balloon has a substantially circular profile at any given point along its length. This profile eliminates the need to know the orientation of the balloon with respect to the lesion or the effects of a non-circular geometry on artery trauma. The invention also exhibits a low crossing profile when compared with perfusion catheters that require a channel within the balloon for blood flow, which increases the crossing profile.

Another advantage of the spiral geometry is that there is no need to rotate the balloon in the artery to ensure that the entire surface of the lesion is dilated as is required in balloons having non-circular profiles. Precisely rotating the balloon of prior art may be quite difficult due to the length of the flexible tube utilized. On the other hand, the present invention need only be advanced or retracted to a small extent, if at all, in the longitudinal direction within the body vessel to effectively dilate the entire surface of the stenosis. The inclusion of the membrane or sheath reduces the likelihood that such movement would be needed.

Yet another advantage of the spiral geometry is that the blood is perfused past the balloon and to peripheral sidebranches of the body vessel. This is particularly advantageous for sidebranches of the artery which are located very close to the restriction or stenosis in the main body vessel which would be sealed off by a standard balloon during an angioplasty procedure.

When utilizing the catheter made according to the present invention, a guidewire typically is first inserted into the body vessel. This can be facilitated when the catheter is of the dual lumen type as discussed herein or the coaxial type. The catheter may then be inserted over the guidewire wherein the guidewire extends through lumen to assist in positioning the catheter in the body vessel. After the perfusion catheter has performed its function of dilating the restricted artery or the like, the balloon may be deflated and the catheter removed.

It will thus be seen that the present invention provides a new and useful perfusion balloon catheter having a number of advantages and characteristics, including those pointed out herein and others which are inherent in the invention. Preferred embodiments of the invention have been described by way of example, and it is anticipated that modifications may be made to the described form without departing from the spirit of the invention or the scope of the appended claims.

We claim:

1. A dilation catheter for use in medical procedures comprising: an elongated flexible tubular member; a dilating balloon disposed on said tubular member, said balloon member having an interior and exterior surface, said balloon having a collapsed condition of a size allowing said balloon to be transported through a body vessel, and said balloon having an expanded condition of a size allowing said exterior surface to engage a body vessel wall; a longitudinally extending spiral wall formed integrally with said exterior surface, said spiral wall defining a longitudinally extending spiral channel spaced radially inwardly from said exterior surface when said balloon is in its expanded condition; and means for passing fluid between said balloon member and said tubular member to vary said balloon member between its collapsed and expanded conditions;

further including a membrane disposed over said longitudinally extending spiral channel, said membrane sealingly connected to the exterior surface of said balloon, and said membrane includes a perforation therethrough at said spiral channel.

2. The dilation catheter of claim 1, wherein said means for passing fluid between said balloon member and said flexible tubing includes at least one pathway between said flexible tubular member and said balloon member.

3. The dilation catheter of claim 1, wherein said flexible tubular member includes a first lumen for transporting a fluid and a second lumen for receiving a guidewire.

4. The dilation catheter of claim 1, wherein said flexible tubular member is a coaxial tube having an inner lumen for receiving a guidewire and an outer lumen for transporting a fluid.

5. The dilation catheter of claim 1, wherein said exterior surface is radially spaced from said tubular member when said balloon member is in its expanded condition.

6. The dilation catheter of claim 1, wherein said exterior surface is substantially adjacent said tubular member when said balloon member is in its collapsed condition.

7. The dilation catheter of claim 1, wherein said exterior surface has a generally spiral configuration defined at least in part by said spiral channel.

8. The dilation catheter of claim 1, wherein said balloon member is in seal tight communication with said flexible tubular member at the distal and proximal ends of said balloon member.

9. The dilation catheter of claim 1, including a plurality of longitudinally extending spiral walls formed integrally with said exterior surface, each of said plurality of spiral walls defining a longitudinally extending spiral channel spaced radially inwardly from said exterior surface when said balloon is in its expanded condition.

10. A method of performing percutaneous transluminal angioplasty procedures utilizing a dilation catheter, wherein said method comprises the steps of: providing a dilation catheter having an elongated flexible tubular member having an extensible balloon disposed on said tubular member, said balloon including an exterior surface and inflatable between a collapsed condition of a size allowing said dilation catheter to be transported through a body vessel and an expanded condition of a size allowing said exterior surface to engage a body vessel wall, said exterior surface including a longitudinally extending spiral wall forming a longitudinally extending spiral channel spaced radially inwardly from said exterior surface when said balloon is in its expanded condition and a membrane disposed over the longitudinally extending spiral channel, the membrane having a perforation therethrough;

inserting said dilation catheter in its collapsed condition into a body vessel; positioning said balloon adjacent a stenosis or restriction in said body vessel; inflating said balloon to its expanded condition for a predetermined period of time to a sufficient size so that said exterior surface engages said stenosis while simultaneously perfusing blood through said spiral channel, including through the perforation of the membrane; and deflating said balloon to its collapsed condition.

11. The method of claim 10, further including moving said balloon longitudinally; and reinflating said balloon to its expanded condition for a predetermined period of time to a sufficient size so that said exterior surface engages said stenosis to ensure that the entire inner circumference of the stenosis has been engaged by said balloon, while simultaneously perfusing blood through said spiral channel.

12. The method of claim 11, wherein said moving step moves the catheter distally through a longitudinal distance slightly greater than the width of the spiral channel.

13. The method of claim 11, wherein said moving step moves the catheter proximally through a longitudinal distance slightly greater than the width of the spiral channel.

\* \* \* \* \*